US008796013B2

(12) United States Patent
Geisbert

(10) Patent No.: US 8,796,013 B2
(45) Date of Patent: Aug. 5, 2014

(54) PRE-OR POST-EXPOSURE TREATMENT FOR FILOVIRUS OR ARENAVIRUS INFECTION

(75) Inventor: Thomas W. Geisbert, Boston, MA (US)

(73) Assignees: Trustees of Boston University, Boston, MA (US); Boston Medical Center Corporation, Boston, MA (US)

( * ) Notice: Subject to any disclaimer, the term of this patent is extended or adjusted under 35 U.S.C. 154(b) by 702 days.

(21) Appl. No.: 12/809,348

(22) PCT Filed: Dec. 17, 2008

(86) PCT No.: PCT/US2008/013787
§ 371 (c)(1),
(2), (4) Date: Sep. 16, 2010

(87) PCT Pub. No.: WO2009/116982
PCT Pub. Date: Sep. 24, 2009

(65) Prior Publication Data
US 2011/0014227 A1    Jan. 20, 2011

Related U.S. Application Data

(60) Provisional application No. 61/014,626, filed on Dec. 18, 2007.

(51) Int. Cl.
*C12N 15/00* (2006.01)
*A61K 39/12* (2006.01)
(52) U.S. Cl.
USPC .................................. 435/320.1; 424/204.1
(58) Field of Classification Search
None
See application file for complete search history.

(56) References Cited

U.S. PATENT DOCUMENTS

| | | |
|---|---|---|
| 2002/0155127 A1 | 10/2002 | Wang |
| 2005/0255123 A1 | 11/2005 | Wilson et al. |
| 2005/0260601 A1 | 11/2005 | Whitt et al. |
| 2006/0269572 A1 | 11/2006 | Nabel et al. |
| 2007/0082011 A1 | 4/2007 | Lehrer et al. |
| 2007/0185025 A1* | 8/2007 | Palacios et al. .................. 514/12 |

FOREIGN PATENT DOCUMENTS

| | | |
|---|---|---|
| EP | 1527087 | 5/2005 |
| JP | 2007516968 A | 6/2007 |
| WO | WO 2004/011488 | 2/2004 |

OTHER PUBLICATIONS

Bausch et al., "Development of Vaccines for Marburg Hemorrhagic Fever," *Expert Rev. Vaccines* 6:57-74, 2007.
Bausch et al., "Outbreaks of Filovirus Hemorrhagic Fever: Time to Refocus on the Patient," *J. Infect. Dis.* 196:S136-141, 2007.
Daddario-DiCaprio et al., "Cross-Protection Against Marburg Virus Strains by Using Live, Attenuated Recombinant Vaccine," *J. Virol.* 80:9659-9666, 2006.
Daddario-DiCaprio et al., "Postexposure Protection Against Marburg Haemorrhagic Fever with Recombinant Vesicular Stomatitis Virus Vectors in Non-Human Primates: An Efficacy Assessment," *Lancet* 367:1399-1404, 2006.
Feldmann et al., "Therapy and Prophylaxis of Ebola Virus Infections," *Curr Opin. Investig. Drugs*, 6:823-830, 2005.
Feldmann et al., "Effective Post-Exposure Treatment of Ebola Infection," *PLoS Pathog.* 3:e2, 2007.
Garbutt et al., "Properties of Replication-Competent Vesicular Stomatitis Virus Vectors Expressing Glycoproteins of Filoviruses and Arenaviruses," *J. Virol.* 78:5458-5465, 2004.
Geisbert et al., "Evaluation in Nonhuman Primates of Vaccines Against Ebola Virus," *Emerg. Infect. Dis.* 8:503-507, 2002.
Geisbert et al., "Evidence Against an Important Role for Infectivity-Enhancing Antibodies in Ebola Virus Infections," *Virology* 293:15-19, 2002.
Geisbert and Jahrling, "Towards a Vaccine Against Ebola Virus," *Expert Rev. Vaccines* 2:89-101, 2003.
Geisbert and Hensley, "Ebola Virus: New Insights into Disease Aetiopathology and Possible Therapeutic Interventions," *Expert Rev. Mol. Med.* 6:1-24, 2004.
Geisbert et al., "Development of a New Vaccine for the Prevention of Lassa Fever," *PLOS Med.* 2:e183, 2005.
Geisbert et al., "Recombinant Vesicular Stomatitis Virus Vector Mediates Postexposure Protection Against Sudan Ebola Hemorrhagic Fever in Nonhuman Primates," *J. Virol.* 82:5664-5668, 2008.
Geisbert et al., "Vesicular Stomatitis Virus-based Ebola Vaccine is Well-tolerated and Protects Immunocompromised Nonhuman Primates," *PLoS Pathog.* 4:e1000225, 2008.
Geisbert et al., "Vesicular Stomatitis Virus-Based Vaccines Protect Nonhuman Primates Against Aerosol Challenge with Ebola and Marburg Viruses," *Vaccine* 26:6894-6900, 2008.
Geisbert et al., "Single-Injection Vaccine Protects Nonhuman Primates Against Infection with Marburg Virus and Three Species of Ebola Virus," *J. Virol.* 83:7296-7304, 2009.
Geisbert et al., "Postexposure Treatment of Marburg Virus Infection," *Emerg. Infect. Dis.* 16:1119-1122 (2010).
Geisbert et al., "Prospects for Immunisation Against Marburg and Ebola Viruses," *Rev. Med. Virol.* 20:344-357, 2010.
Geisbert et al., "Vector Choice Determines Immunogenicity and Potency of Genetic Vaccines Against Angola Marburg Virus in Nonhuman Primates," *J. Virol.* 84:10386-10394, 2010.
GenBank Accession No. U28006, submitted Oct. 27, 1995.
Gibb et al., "Pathogenesis of Experimental Ebola Zaire Virus Infection in BALB/c Mice," *J. Comp. Pathol.* 125:233-242, 2001.
Hensley et al., "Ebola and Marburg Viruses: Pathogenesis and Development of Countermeasures," *Curr. Mol. Med.* 5:761-772, 2005.
Hevey et al., "Antigenicity and vaccine potential of Marburg virus glycoprotein expressed by baculovirus recombinants," *Virology* 239:206-216, 1997.
Hevey et al., "Marburg Virus Vaccines: Comparing Classical and New Approaches," *Vaccine* 20:586-593, 2002.

(Continued)

*Primary Examiner* — Stacey B. Chen
(74) *Attorney, Agent, or Firm* — Clark & Elbing LLP; Paul T. Clark; Todd Armstrong

(57) ABSTRACT

The compositions and methods of the invention described herein provide pre- or post-exposure treatments against filovirus or arenavirus infection by expressing one or more genes (e.g., two ore more genes) from filoviruses or arenaviruses in a delivery vehicle (e.g., a recombinant viral vector or a liposome).

13 Claims, 7 Drawing Sheets

(56) References Cited

OTHER PUBLICATIONS

Holman et al., "Two Complex, Adenovirus-based Vaccines that Together Induce Immune Responses to All Four Dengue Virus Serotypes," *Clin. Vacc. Immunol.* 14:182-189, 2007.

Holman et al., "Multi-Antigen Vaccines Based on Complex Adenovirus Vectors Induce Protective Immune Responses against H5N1 Avian Influenza Viruses," *Vaccine* 26:2627-2639, 2008.

Jones et al., "Live Attenuated Recombinant Vaccine Protects Nonhuman Primates Against Ebola and Marburg Viruses," *Nat. Med.* 11:786-790, 2005.

Marty et al.,"Viral Hemorrhagic Fevers," *Clin. Lab. Med.* 26:345-386, 2006.

Mellquist-Riemenschneider et al., "Comparison of the Protective Efficacy of DNA and Baculovirus-Derived Protein Vaccines for Ebola Virus in Guinea Pigs," *Virus Res.* 92:187-193, 2003.

Pushko et al., "Individual and Bivalent Vaccines Based on Alphavirus Replicons Protect Guinea Pigs Against Infection with Lassa and Ebola Viruses," *J. Virol.* 75:11677-11685, 2001.

Riemenschneider et al., "Comparison of Individual and Combination DNA Vaccines for *B. Anthracis*, Ebola Virus, Marburg Virus and Venezuelan Equine Encephalitis Virus," *Vaccine* 21:4071-4080, 2003.

Sanchez et al., "The Virion Glycoproteins of Ebola Viruses are Encoded in Two Reading Frames and are Expressed through Transcriptional Editing," *Proc. Nat'l, Acad. Sci. USA* 93:3602-3607, 1996.

Schepp-Berglind et al., "Complex Adenovirus-Mediated Expression of West Nile Virus C, PreM, E, and NS1 Proteins Induces both Humoral and Cellular Immune Responses," *Clin. Vacc. Immunol.* 14:1117-1126, 2007.

Sullivan et al., "Accelerated Vaccination for Ebola Virus Haemorrhagic Fever in Non-Human Primates," *Nature* 424:681-684, 2003.

Sullivan et al., "Immune Protection of Nonhuman Primates Against Ebola Virus with Single Low-Dose Adenovirus Vectors Encoding Modified GPs," *PLoS Med.* 3:e177, 2006.

Swenson et al. "Vaccine to Confer to Nonhuman Primates Complete Protection against Multistrain Ebola and Marburg Virus Infections," *Clin. Vacc. Immunol.* 15:460-467, 2008.

Takada et al., "Epitopes Required for Antibody-Dependent Enhancement of Ebola Virus Infection," *J. Infect. Dis.* 196:S347-S356 (2007).

Wang et al., "Complex Adenovirus-Vectored Vaccine Protects Guinea Pigs from Three Strains of Marburg Virus Challenges," *Virol.* 353:324-332, 2006.

Wang et al., "De Novo Syntheses of Marburg Virus Antigens from Adenovirus Vectors Induce Potent Humoral and Cellular Immune Responses," *Vaccine* 24:2975-2986, 2006.

International Search Report for PCT/US2009/001821 mailed on Aug. 6, 2009.

International Search Report for PCT/US2008/13798 mailed Aug. 31, 2009.

International Search Report for PCT/US2008/13787 mailed on Oct. 20, 2009.

International Preliminary Report on Patentability for PCT/US2008/13787 (completion date Oct. 6, 2009; mailed on Jun. 22, 2010).

International Preliminary Report on Patentability for PCT/US2008/13798 (completion date Aug. 18, 2009; mailed on Jun. 22, 2010).

International Preliminary Report on Patentability for PCT/US2009/001821 (completion date May 8, 2009; mailed on Sep. 28, 2010).

Supplementary European Search Report for European Patent Application No. 08873458.7 dated Nov. 7, 2012.

Casillas et al., "A current review of Ebola virus: pathogenesis, clinical presentation, and diagnostic assessment," Biol Res Nurs. 4(4):268-75 (Abstract only) (2003).

Dye et al., "Postexposure antibody prophylaxis protects nonhuman primates from filovirus disease," Proc Natl Aced Sci USA. 109(13):5034-9 (2012).

Ebola and marburg hemorrhagic fevers: African hemorrhagic fever, Iowa State University Jan. 9, 2009.

Qiu et al., "Successful treatment of ebola virus-infected cynomolgus macaques with monoclonal antibodies," Sci Transl Med. 4(138):1-11 (2012).

English Translation of Notification of Reason for Rejection for Japanese Patent Application No. 2010-539467, mailed Aug. 20, 2013 (5 pages).

* cited by examiner

Fig. 1

| Animal | Day 1-5 | Day 6 | Day 7-9 | Day 10 | Day 14 | Day 22 | Day of Death |
|---|---|---|---|---|---|---|---|
| Subject 1 | | Fever, anorexia, lymphopenia, thrombocytopenia, AST↑ | Anorexia | Lymphopenia, thrombocytopenia, ALT↑↑↑, AST↑↑↑, BUN↑↑↑, CRE↑↑↑, GGT↑ | Thrombocytopenia, AST↑ | | Survived |
| Subject 2 | | Fever | | | | | Survived |
| Subject 3 | | Fever, anorexia, lymphopenia, AST↑ | Moderate rash, anorexia | | NA | NA | Day 9 |
| Subject 4 | | Fever, anorexia | Moderate rash, anorexia | | NA | NA | Day 10 |
| Subject 5 | | Fever, lymphopenia | Anorexia | Thrombocytopenia, GGT↑ | GGT↑ | NA | Survived |
| Subject 6 | | Fever, lymphopenia | Anorexia | Anorexia, thrombocytopenia, ALT↑, AST↑↑ | Anorexia, lymphopenia | NA | Day 18 |
| Subject 7 | | Fever, lymphopenia | | | | | Survived |
| Subject 8 | | Fever, anorexia, lymphopenia, thrombocytopenia | Moderate rash, anorexia | Severe rash, thrombocytopenia, ALP↑, ALT↑↑↑, AST↑↑↑, BUN↑↑↑, CRE↑, GGT↑↑ | NA | NA | Day 10 |
| Control 1 | | Fever, mild rash, lymphopenia | Moderate rash, anorexia, thrombocytopenia, ALP↑, ALT↑↑, AST↑↑↑, BUN↑, CRE↑, GGT↑↑ | NA | NA | NA | Day 8 |
| Control 2 | | Fever, lymphopenia, ALT↑, AST↑ | Severe rash, anorexia | NA | NA | NA | Day 8 |

Fever is defined as a temperature more than 2.5 °F over baseline or at least 1.5 °F over baseline and ≥103.5 °F.
Mild rash: focal areas of petechiae covering less than 10% of the skin; moderate rash: areas of petechiae covering between 10% and 40% of the skin; severe rash: areas of petechiae or ecchymosis covering more than 40% of the skin.
Lymphopenia and thrombocytopenia defined by ≥35% drop in numbers of lymphocytes and platelets, respectively.
Phlebotomy was performed and rectal temperatures were recorded on days 3, 6, 10, 14, and 22 with the exception of control 1, where phlebotomy and rectal temperature were also taken on day 8 at the time of euthanasia.
↑, 2- to 3-fold increase; ↑↑, 4- to 5-fold increase; ↑↑↑, >5-fold increase.
ALP, alkaline phosphatase; ALT, alanine aminotransferase or serum glutamic-pyruvic transaminase (sGPT); AST, aspartate aminotransferase or serum glutamic-oxaloacetic transaminase (sGOT); BUN, blood urea nitrogen; CRE, creatinine; GGT, gamma-glutamyl transferase or gamma-glutamyl transpeptidase; NA, not applicable, as the animal had succumbed to EBOV challenge.
doi:10.1371/journal.ppat.0030002.t001

-☒- Control animals treated with VSVΔG/ZEBOVGP vectors
-△- Animals treated with VSVΔG/MARVGP vectors

Fig. 5

|  | VSV-MARV-treated animals | | | | | Control animals | | |
| --- | --- | --- | --- | --- | --- | --- | --- | --- |
|  | 1 | 2 | 3 | 4 | 5 | 6 | 7 | 8 |
| Day 3 | 0 | 0 | 0 | 0 | 0 | 0 | 0 | 0 |
| Day 6 | 0 | 0 | 0 | 0 | 0 | 3.2 | 3.7 | 5.5 |
| Day 10 | 0 | 0 | 0 | 0 | 0 | 7.5 | 7.5 | 6.4 |
| Day 11 | 0 | 0 | 0 | 0 | 0 | 7.0 | 7.4 | 6.9* |

Viraemia measured as MARV titres $\log_{10}$ pfu/mL. Days indicate period after MARV challenge. *Measured on day 12.

Fig. 6

|  | VSV-MARV-treated animals | | | | | Control animals | | |
|---|---|---|---|---|---|---|---|---|
|  | 1 | 2 | 3 | 4 | 5 | 6 | 7 | 8 |
| IgM response profile | | | | | | | | |
| Day 3 | 0 | 0 | 0 | 0 | 0 | 0 | 0 | 0 |
| Day 6 | 32 | 100 | 100 | 32 | 32 | 0 | 0 | 0 |
| Day 10 | 100 | 32 | 0 | 32 | 32 | 0 | 0 | 0 |
| Day 14 | 0 | 32 | 0 | 0 | 100 | .. | .. | .. |
| IgG response profile | | | | | | | | |
| Day 6 | 32 | 0 | 0 | 0 | 0 | 0 | 0 | 0 |
| Day 10 | 1000 | 320 | 0 | 100 | 100 | 0 | 0 | 0 |
| Day 14 | 1000 | 3200 | 32 | 320 | 100 | .. | .. | .. |
| Day 22 | 320 | 3200 | 32 | 320 | 1000 | .. | .. | .. |
| Day 37 | 320 | 320 | 100 | 320 | 1000 | .. | .. | .. |

Data are endpoint dilution titres. Days indicate period after MARV challenge.

Fig. 7

VSV-MARV-treated animals

PRE- OR POST-EXPOSURE TREATMENT FOR FILOVIRUS OR ARENAVIRUS INFECTION

CROSS-REFERENCE TO RELATED APPLICATIONS

This application is the U.S. National Stage of International Application PCT/US2008/013787, filed Dec. 17, 2008, which claims benefit of U.S. Provisional Application Ser. No. 61/014,626, filed Dec. 18, 2007.

BACKGROUND OF THE INVENTION

Infection with the filoviruses, in particular Zaire ebolavirus (ZEBOV), Sudan ebolavirus, or Marburg virus (MARV), causes severe hemorrhagic fever (HF) in humans and nonhuman primates that is often fatal. In addition to the sporadic outbreaks that have occurred in humans in Central Africa since 1976 and have caused more than 1,800 human infections with a lethality rate ranging from 53% to 90%, Ebola virus (EBOV) has also decimated populations of wild apes in this same region. At this time, there is no preventive vaccine or post-exposure treatment option available for human use. Much remains to be learned about these highly virulent viruses; however, important advances have been made over the last decade in understanding how filoviruses cause disease and in developing preventive vaccines that are protective in nonhuman primates. There still remains an urgent need to develop filovirus-specific post-exposure strategies to respond to future outbreaks of these viruses and to counter acts of bioterrorism.

SUMMARY OF THE INVENTION

The compositions and methods of the invention described herein provide pre- and/or post-exposure treatments against filovirus and arenavirus infection by expressing one or more genes (e.g., two or more genes) from one or more filoviruses or arenaviruses, respectively, in a delivery vehicle (e.g., a recombinant viral vector or a liposome). In one embodiment, the pharmaceutical composition of the invention includes a recombinant viral vector that includes at least one gene (e.g., the glycoprotein gene) from the Zaire species of Ebola virus (ZEBOV) (e.g., the Mayinga strain, GenBank No. AAN37507), the Sudan species of Ebola virus (SEBOV) (e.g., the Gulu strain, GenBank No. AY316199; the Boniface strain, GenBank No. U28134; or the Maleo strain, GenBank No. U23069), Marburg virus (MARV) (e.g., the Musoke strain, GenBank No. YP_001531156), or Lassa virus (e.g., the Josiah strain, GenBank No. NP_694870). In another embodiment, the delivery vehicle includes at least one polypeptide (e.g., the Ebola virus glycoprotein) from the Zaire species of Ebola virus (ZEBOV) (e.g., the Mayinga strain, GenBank No. AAN37507), the Sudan species of Ebola virus (SEBOV) (e.g., the Gulu strain, GenBank No. AY316199; the Boniface strain, GenBank No. U28134; or the Maleo strain, GenBank No. U23069), Marburg virus (MARV) (e.g., the Musoke strain, GenBank No. YP_001531156), or Lassa virus (e.g., the Josiah strain, GenBank No. NP_694870). The pharmaceutical composition may further include a pharmaceutically acceptable diluent, excipient, carrier, or adjuvant. In an embodiment, the viral vector is a recombinant vesicular stomatitis virus (rVSV) vector that includes or encodes all of part of, e.g., an Ebola virus glycoprotein. The pharmaceutical composition may be, e.g., a vaccine. The vaccine may inhibit infection by, e.g., a filovirus or arenavirus (e.g., ZEBOV, SEBOV, ICEBOV, MARV, or Lassa virus). The pharmaceutical composition may also alleviate the symptoms (e.g., fever, hemorrhagic fever, severe headache, muscle pain, malaise, extreme asthenia, conjunctivitis, popular rash, dysphagia, nausea, vomiting, bloody diarrhea followed by diffuse hemorrhages, delirium, shock, jaundice, thrombocytopenia, lymphocytopenia, neutrophilia, focal necrosis in various organs (e.g., kidneys and liver), and acute respiratory distress) associated with filovirus or arenavirus infection (e.g., infection by ZEBOV, SEBOV, ICEBOV, MARV, or Lassa virus). The pharmaceutical composition described herein may be administered to a subject infected with, exposed to, or at risk of exposure to a filovirus or arenavirus (e.g., ZEBOV, SEBOV, ICEBOV, MARV, or Lassa virus). The composition may include, e.g., between $1\times10^1$ and $1\times10^8$ pfu of the viral vector, preferably between $1\times10^2$ and $1\times10^8$ pfu, more preferably between $1\times10^3$ and $1\times10^8$ pfu, or most preferably between $1\times10^4$ and $1\times10^8$ pfu. The composition may include, e.g., at least $1\times10^3$ pfu of the viral vector (e.g., $1\times10^4$ pfu of the viral vector). The composition may be administered to a subject, e.g., two or more times.

In another embodiment, the invention features a method of inhibiting or treating a filovirus or arenavirus infection in a subject by administering to the subject a delivery vehicle (e.g., a recombinant viral vector) that encodes at least one gene (e.g., a glycoprotein gene) from a filovirus or arenavirus (e.g., ZEBOV, SEBOV, ICEBOV, MARV, or Lassa virus) in an amount sufficient to treat the infection. The subject being treated may not have, but is at risk of developing, an infection by a filovirus or arenavirus. Alternatively, the subject may already be infected with a filovirus or arenavirus. The subject being treated may be, e.g., a human. The composition may be administered, e.g., by injection (e.g., intramuscular, intraarterial, intravascular, intravenous, intraperitoneal, or subcutaneous injection). The composition of the method may include, e.g., between $1\times10^1$ and $1\times10^8$ pfu of the viral vector, preferably between $1\times10^2$ and $1\times10^8$ pfu, more preferably between $1\times10^3$ and $1\times10^8$ pfu, or most preferably between $1\times10^4$ and $1\times10^8$ pfu. The composition may include, e.g., at least $1\times10^3$ pfu of the viral vector (e.g., $1\times10^4$ pfu of the viral vector). The method may include, e.g., administering the composition to the subject two or more times.

The invention also features a method of inducing an immune response to a filovirus or an arenavirus in a subject by administering to a subject a recombinant viral vector that encodes at least one gene (e.g., a glycoprotein gene) from a filovirus or arenavirus (e.g., ZEBOV, SEBOV, ICEBOV, MARV, or Lassa virus) in an amount sufficient to treat the infection. The subject being treated may not have, but is at risk of developing, an infection by a filovirus or arenavirus. Alternatively, the subject may already be infected with a filovirus or arenavirus. The subject being treated may be, e.g., a human. The composition may be administered, e.g., by injection (e.g., intramuscular, intraarterial, intravascular, intravenous, intraperitoneal, or subcutaneous injection). The composition of the method may include, e.g., between $1\times10^1$ and $1\times10^8$ pfu of the viral vector, preferably between $1\times10^2$ and $1\times10^8$ pfu, more preferably between $1\times10^3$ and $1\times10^8$ pfu, or most preferably between $1\times10^4$ and $1\times10^8$ pfu. The composition may include, e.g., at least $1\times10^3$ pfu of the viral vector (e.g., $1\times10^4$ pfu of the viral vector). The method may include, e.g., administering the composition to the subject two or more times.

As used herein, by "administering" is meant a method of giving a dosage of a pharmaceutical composition to a subject. The compositions utilized in the methods described herein can be administered by a route selected from, e.g., parenteral, dermal, transdermal, ocular, inhalation, buccal, sublingual, perilingual, nasal, rectal, topical administration, and oral administration. Parenteral administration includes intravenous, intraperitoneal, subcutaneous, and intramuscular administration. The preferred method of administration can vary depending on various factors (e.g., the components of the composition being administered and the severity of the condition being treated).

By "an amount sufficient to treat" is meant the amount of a composition administered to improve, inhibit, or ameliorate a condition of a subject, or a symptom of a disorder, in a clinically relevant manner (e.g., improve, inhibit, or ameliorate infection by a filovirus or arenavirus or one or more symptoms that occur following infection). Any improvement in the subject is considered sufficient to achieve treatment. Preferably, an amount sufficient to treat is an amount that prevents the occurrence or one or more symptoms of filovirus or arenavirus infection or is an amount that reduces the severity of, or the length of time during which a subject suffers from, one or more symptoms of the infection (e.g., by at least 10%, 20%, or 30%, more preferably by at least 50%, 60%, or 70%, and most preferably by at least 80%, 90%, 95%, 99%, or more, relative to a control subject that is not treated with a composition of the invention). A sufficient amount of the pharmaceutical composition used to practice the methods described herein (e.g., the treatment of infection) varies depending upon the manner of administration and the age, body weight, and general health of the subject being treated. A physician or researcher can decide the appropriate amount and dosage regimen.

As used herein, the term "gene" refers to a nucleic acid molecule that either directly or indirectly encodes a nucleic acid or protein product that has a defined biological activity.

By "glycoprotein" is meant the glycoprotein polypeptide, in secreted or transmembrane bound form, or any fragment or mutation of the glycoprotein polypeptide that is encoded by the ZEBOV, SEBOV, MARV, or Lassa virus genome so long as it has the ability to induce or enhance an immune response that confers a protective or therapeutic benefit to the subject, e.g., against a filovirus or arenavirus (e.g., ZEBOV, SEBOV, ICEBOV, MARV, or Lassa virus). The glycoprotein may also include any polypeptide that is substantially identical (e.g., at least 60%, 65%, 70%, 75%, 80%, 85%, 90%, 95%, 98%, 99%, or even 100% identical) to the ZEBOV, SEBOV, MARV, or Lassa virus glycoprotein over at least 20, 25, 30, 35, 40, 45, 50, 55, 60, 65, or 70 contiguous residues.

By "inducing an immune response" is meant eliciting a humoral response (e.g., the production of antibodies) or a cellular response (e.g., the activation of T cells) directed against a virus (e.g., filovirus or arenavirus) in a subject to which the pharmaceutical composition (e.g., a vaccine) has been administered.

By "pharmaceutical composition" is meant any composition that contains at least one therapeutically or biologically active agent (e.g., at least one nucleic acid molecule or protein product, in whole or in part, of or corresponding to a filovirus or arenavirus genome, either incorporated into a viral vector or independent of a viral vector) and is suitable for administration to a subject. For the purposes of this invention, pharmaceutical compositions suitable for delivering a therapeutic or biologically active agent can include, e.g., tablets, gelcaps, capsules, pills, powders, granulates, suspensions, emulsions, solutions, gels, hydrogels, oral gels, pastes, eye drops, ointments, creams, plasters, drenches, delivery devices, suppositories, enemas, injectables, implants, sprays, or aerosols. Any of these formulations can be prepared by well-known and accepted methods of art. See, for example, *Remington: The Science and Practice of Pharmacy* (21$^{st}$ ed.), ed. A. R. Gennaro, Lippincott Williams & Wilkins, 2005, and *Encyclopedia of Pharmaceutical Technology*, ed. J. Swarbrick, Informa Healthcare, 2006, each of which is hereby incorporated by reference.

By "pharmaceutically acceptable diluent, excipient, carrier, or adjuvant" is meant a diluent, excipient, carrier, or adjuvant which is physiologically acceptable to the subject while retaining the therapeutic properties of the pharmaceutical composition with which it is administered. One exemplary pharmaceutically acceptable carrier is physiological saline. Other physiologically acceptable diluents, excipients, carriers, or adjuvants and their formulations are known to one skilled in the art.

By "recombinant," with respect to a viral vector, is meant a vector (e.g., a viral genome that has been incorporated into one or more delivery vehicles (e.g., a plasmid, cosmid, etc.)) that has been manipulated in vitro, e.g., using recombinant nucleic acid techniques to introduce changes to the viral genome (e.g., to include heterologous viral nucleic acid sequences). An example of a recombinant viral vector of the invention is a vector that includes all or part of the VSV genome and that includes the nucleic acid sequence for all or part of, e.g., a heterologous viral gene, such as a glycoprotein gene (e.g., the glycoprotein gene of a filovirus or an arenavirus).

By "subject" is meant any animal, e.g., a mammal (e.g., a human).

A subject to be treated according to the methods described herein (e.g., a subject infected with, or at risk of being infected with, a filovirus or arenavirus) may be one who has been diagnosed by a medical practitioner as having such a condition. Diagnosis may be performed by any suitable means. A subject in whom the development of an infection is being prevented may or may not have received such a diagnosis. One skilled in the art will understand that a subject to be treated according to the present invention may have been subjected to standard tests or may have been identified, without examination, as one at high risk due to the presence of one or more risk factors (e.g., exposure to a filovirus, etc.).

By "treating" is meant administering a pharmaceutical composition for prophylactic and/or therapeutic purposes. Prophylactic treatment may be administered, for example, to a subject who is not yet ill, but who is susceptible to, or otherwise at risk of, a particular disorder, e.g., infection with a filovirus or arenavirus. Therapeutic treatment may be administered, for example, to a subject already suffering from a disorder in order to improve or stabilize the subject's condition (e.g., a patient already infected with a filovirus). Thus, in the claims and embodiments described herein, treating is the administration to a subject either for therapeutic or prophylactic purposes. In some instances, as compared with an equivalent untreated control, treatment may ameliorate a disorder or a symptom thereof by, e.g., 5%, 10%, 20%, 30%, 40%, 50%, 60%, 70%, 80%, 90%, 95%, or 100% as measured by any standard technique. In some instances, treating can result in the inhibition of viral infection, the treatment of the infection, and/or the amelioration of symptoms (e.g., hemorrhagic fever) of the infection. Confirmation of treatment can be assessed by detecting an improvement in or the absence of symptoms, or by the inability to detect the presence of a filovirus or arenavirus in the treated subject.

By "viral vector" is meant a composition that includes one or more viral genes from two or more virus species that is able to transmit the genetic information to a host or subject. The nucleic acid material of the viral vector may be encapsulated, e.g., in a lipid membrane or by structural proteins (e.g., capsid proteins), that may include one or more viral polypeptides (e.g., a glycoprotein). The one or more viral genes of the viral vector may include, e.g., a nucleic acid that encodes one or more polypeptides of a filovirus or arenavirus. The viral vector can be used to infect cells of a subject, which, in turn, promotes the translation into a protein product of the one or more viral genes of the viral vector (e.g., a glycoprotein). The viral vector may also be, e.g., a pseudotyped virus that includes one or more of the polypeptides encoded by the genome of the filovirus or arenavirus. The viral vector itself can be used to stimulate an immune response that is protective against infection by a filovirus or arenavirus or that treats infection by a filovirus or arenavirus. Alternatively, the viral vector can be administered to a subject so that it infects one or more cells of the subject, which then promotes expression of the one or more viral genes of the viral vector and stimulates an immune response that is protective against infection by a filovirus or arenavirus or that treats infection by a filovirus or arenavirus.

The term "vaccine," as used herein, is defined as material used to provoke an immune response and confer immunity after administration of the vaccine to a subject.

Other features and advantages of the invention will be apparent from the detailed description and from the claims.

BRIEF DESCRIPTION OF THE DRAWINGS

FIG. 1 is a table showing the clinical findings of rhesus monkeys treated with the VSVΔG/ZEBOVGP vaccine or treated with the VSV control vaccine.

FIG. 2 is a graph showing the survival and plasma viraemia for rhesus monkeys given post-exposure treatment for ZEBOV infection. Figure (A) shows Kaplan-Meier survival curves for animals treated with $2 \times 10^7$ pfu of VSVΔG/ZEBOVGP (subjects 1 to 8, solid line) or VSV control vectors (subjects c1 and c2, dotted line) 20-30 min after i.m. challenge with 1,000 pfu of ZEBOV. Figure (B) shows plasma viraemia of animals treated with VSVΔG/ZEBOVGP or VSV control vectors 20-30 min after i.m. challenge with 1,000 pfu of ZEBOV. Viraemia was determined by plaque assay at indicated time points. The asterisk indicates that on day 8 post-challenge viraemia levels were only determined for the control animals (subjects c1 and c2). Plasma viraemia levels at day 6 post-ZEBOV challenge could be separated into three different groups. Control animals, which received VSV control vectors (black square), developed high plasma viraemias ($>6 \log_{10}$ pfu/ml). Animals treated with VSVΔG/ZEBOVGP, which developed fulminant EBOV HF and succumbed to ZEBOV challenge (orange square), developed moderate plasma viraemias (4-6 $\log_{10}$ pfu/ml), while animals treated with VSVΔG/ZEBOVGP, which survived (green square), had low plasma viraemias (1.4 $\log_{10}$ pfu/ml). Subject 6 did not develop fulminant disease consistent with EBOV HF and succumbed on day 18 from a secondary bacterial infection.

FIG. 4 is a Kaplan-Meier survival curve of rhesus monkeys treated with rVSV vectors after MARV challenge. The control animals (■) were treated with VSVΔG/ZEBOVGP vectors. The experimental group (▲) was treated with a VSVΔG/MARVGP vector.

FIG. 5 is a table showing the plasma viraemia of non-human primates after challenge with MARV and treatment with rVSV vectors.

FIG. 6 is a table showing the serological response profiles of MARV infection after treatment with VSVΔG/MARVGP vectors.

FIG. 7 is a graph showing the development of neutralizing antibodies in animals treated with VSVΔG/MARVGP after MARV challenge.

DETAILED DESCRIPTION

Figure 3:
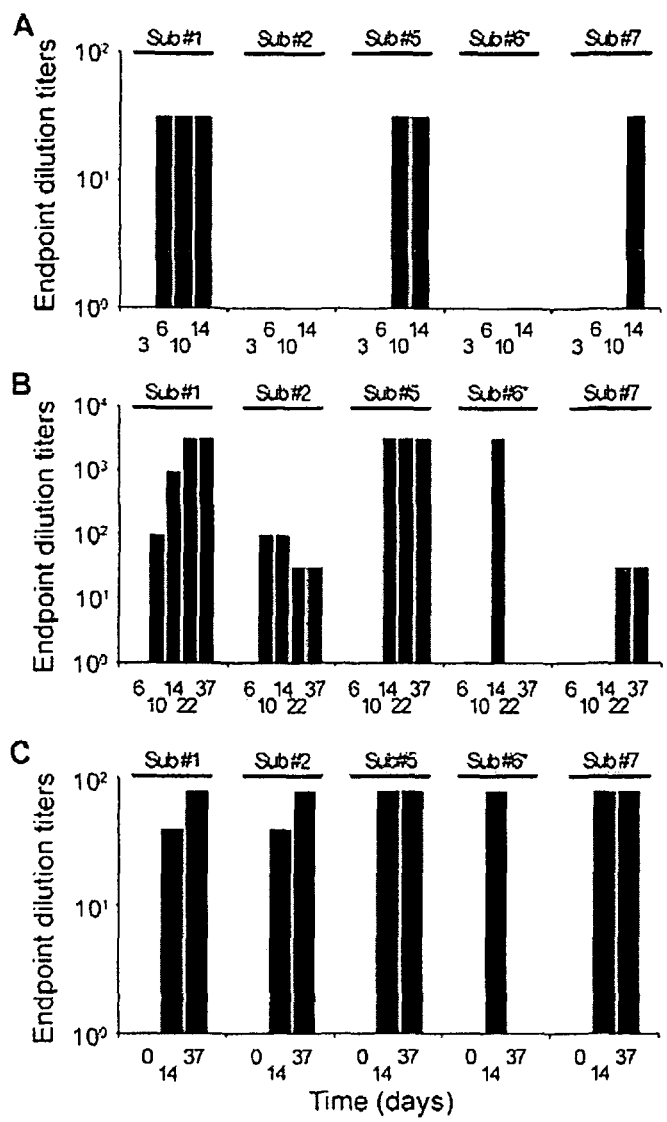
FIG. 3 is a serological response profile for rhesus monkeys given post-exposure treatment for ZEBOV infection. The figures show IgM (A), IgG (B), and development of EBOV-neutralizing antibodies (C) in sera of animals treated with $2 \times 10^7$ pfu of VSVΔG/ZEBOVGP 20-30 min after i.m. challenge with 1,000 pfu of ZEBOV.

The present invention described herein provides compositions and methods for their use for pre- and/or post-exposure treatments against filovirus or arenavirus infection. The compositions of the invention include delivery vehicles (e.g., viral vectors or liposomes) that include one or more filovirus or arenavirus polypeptides (e.g., the glycoprotein) present on the surface of the delivery vehicle. The invention also includes delivery vehicles (e.g., viral vectors or liposomes) that include one or more filovirus or arenavirus genes (e.g., the glycoprotein gene), which can be expressed in a cell of a subject exposed to the delivery vehicle. In both instances, the delivery vehicle promotes the development of an immune response that protects a subject from filovirus or arenavirus infection, either pre- or post-exposure.

Filoviruses

Infection with the filoviruses causes severe hemorrhagic fever in humans and nonhuman primates that is often fatal. The compositions and methods described herein utilize a gene or genes from the filoviruses (e.g., ZEBOV, SEBOV, MARV) or from arenaviruses (e.g., the Lassa virus) to confer protection against pathogenic species of filoviruses or an arenavirus. The gene(s) encoded on the viral vector of the invention may be, e.g., a glycoprotein gene, or a fragment thereof, that has the ability to induce or enhance an immune response that confers a protective or therapeutic benefit to the subject. The glycoprotein may have a mutation or deletion (e.g., an internal deletion, truncation of the amino- or carboxy-terminal, or a point mutation), so long as the mutation or deletion does not interfere with the immune response elicited by the glycoprotein upon administration. The glycoprotein polypeptide or fragment capable of eliciting an immune response may have 5, 6, 7, 8, 9, 10, 20, 25, 30, 40, 50, 60, 70, 80, 90, 100, 125, 150, 175, 200, 300, 400, 500, 600 or more amino acid residues.

The sequences encoding the glycoprotein may be obtained by any suitable means, including, e.g., application of genetic engineering techniques to a viral source, chemical synthesis techniques, recombinant production, or any combination thereof. The sequences of the filoviruses are published and are available from a variety of sources, including, e.g., GenBank and PubMed (e.g., GenBank No. AF272001 for the ZEBOV Mayinga strain or GenBank No. Z12132 for the MARV Musoke strain).

Viral Vectors

In the invention described herein, a viral vector is utilized for the delivery of the pharmaceutical composition. Any suitable viral vector system can be used including, e.g., adenoviruses, rhabdoviruses (e.g., vesicular stomatitis virus), or poxviruses. The viral vector may be constructed using conventional techniques known to one of skill in the art. For example, the viral vector may contain at least one sequence encoding a gene from, e.g., ZEBOV, SEBOV, ICEBOV, MARV, or Lassa virus (e.g., a glycoprotein gene), which is under the control of regulatory sequences that direct its expression in a cell. Appropriate amounts for vector-mediated delivery of the, e.g., filovirus glycoprotein gene can be readily determined by one of skill in the art, based on the information provided herein.

Non-Viral Vectors

Non-viral approaches can also be employed for the introduction of therapeutic nucleic acid molecules or proteins into cells to treat or prevent filovirus or arenavirus infection. For example, a glycoprotein, or nucleic acid molecule encoding the same, from a filovirus or arenavirus can be introduced into a cell by lipofection (see, e.g., Felgner et al., *Proc. Natl. Acad. Sci. USA* 84:7413, 1987; Ono et al., *Neuroscience Letters* 17:259, 1990; Brigham et al., *Am. J. Med. Sci.* 298:278, 1989; Staubinger et al., *Methods in Enzymology* 101:512, 1983), asialoorosomucoid-polylysine conjugation (Wu et al., *Journal of Biological Chemistry* 263:14621, 1988; Wu et al., *Journal of Biological Chemistry* 264:16985, 1989), or, less preferably, micro-injection under surgical conditions (Wolff et al., *Science* 247:1465, 1990). Gene transfer can also be achieved by the use of calcium phosphate, DEAE dextran, electroporation, and protoplast fusion. Liposomes, microparticles, or nanoparticles can also be potentially beneficial for delivery of a nucleic acid molecule or a protein (e.g., a gene that encodes a filovirus or an arenavirus glycoprotein or the glycoprotein encoded thereby) into a cell or into a patient in order to stimulate an immune response against the nucleic acid molecule or polypeptide.

Therapy

Therapy according to the methods described herein may be performed alone or in conjunction with another therapy, and may be provided, e.g., at home, the doctor's office, a clinic, a hospital's outpatient department, or a hospital. Treatment generally begins at a hospital so that the doctor can observe the therapy's effects closely and make any adjustments that are needed. The duration of the therapy depends on the age and condition of the subject, the severity of the subject's infection, and how the subject responds to the treatment.

Formulation and Administration of the Pharmaceutical Composition

The compositions utilized in the methods described herein can be administered by a route selected from, e.g., parenteral, dermal, transdermal, ocular, inhalation, buccal, sublingual, perilingual, nasal, topical administration, and oral administration. The preferred method of administration can vary depending on various factors (e.g., the components of the composition being administered and the severity of the condition being treated). Formulations suitable for oral administration may consist of liquid solutions, such as an effective amount of the composition dissolved in a diluent (e.g., water, saline, or PEG-400), capsules, sachets or tablets, each containing a predetermined amount of the vaccine. The pharmaceutical composition may also be an aerosol formulation for inhalation, e.g., to the bronchial passageways. Aerosol formulations may be mixed with pressurized, pharmaceutically acceptable propellants (e.g., dichlorodifluoromethane, propane, or nitrogen).

Immunogenicity of the composition (e.g., vaccine) may be significantly improved if the composition of the present invention is co-administered with an immunostimulatory agent or adjuvant. Suitable adjuvants well-known to those skilled in the art include, e.g., aluminum phosphate, aluminum hydroxide, QS21, Quil A (and derivatives and components thereof), calcium phosphate, calcium hydroxide, zinc hydroxide, glycolipid analogs, octodecyl esters of an amino acid, muramyl dipeptides, polyphosphazene, lipoproteins, ISCOM matrix, DC-Chol, DDA, cytokines, and other adjuvants and derivatives thereof.

In some instances, it may be desirable to combine the compositions of the present invention with compositions that induce protective responses against other viruses. For example, the compositions of the present invention can be administered simultaneously, separately, or sequentially with other immunization vaccines, such as those for, e.g., influenza, malaria, tuberculosis, or any other vaccines known in the art.

Pharmaceutical compositions according to the invention described herein may be formulated to release the composition immediately upon administration (e.g., targeted delivery) or at any predetermined time period after administration using controlled or extended release formulations. Administration of the pharmaceutical composition in controlled or extended release formulations is useful where the composition, either alone or in combination, has (i) a narrow therapeutic index (e.g., the difference between the plasma concentration leading to harmful side effects or toxic reactions and the plasma concentration leading to a therapeutic effect is small; generally, the therapeutic index, TI, is defined as the ratio of median lethal dose ($LD_{50}$) to median effective dose ($ED_{50}$)); (ii) a narrow absorption window in the gastro-intestinal tract; or (iii) a short biological half-life, so that frequent dosing during a day is required in order to sustain a therapeutic level.

Many strategies can be pursued to obtain controlled or extended release in which the rate of release outweighs the rate of metabolism of the pharmaceutical composition. For example, controlled release can be obtained by the appropriate selection of formulation parameters and ingredients, including, e.g., appropriate controlled release compositions and coatings. Suitable formulations are known to those of skill in the art. Examples include single or multiple unit tablet or capsule compositions, oil solutions, suspensions, emulsions, microcapsules, microspheres, nanoparticles, patches, and liposomes.

Administration of the pharmaceutical compositions (e.g., vaccines) of the present invention can be by any of the routes known to one of skill in the art. Administration may be by, e.g., intramuscular injection. The compositions utilized in the methods described herein can also be administered by a route selected from, e.g., parenteral, dermal, transdermal, ocular, inhalation, buccal, sublingual, perilingual, nasal, rectal, topical administration, and oral administration. Parenteral administration includes intravenous, intraperitoneal, subcutaneous, and intramuscular administration. The preferred method of administration can vary depending on various factors, e.g., the components of the composition being administered and the severity of the condition being treated. The composition may be administered as a vaccine or after a subject has been exposed to a filovirus or an arenavirus. The composition may be administered, e.g., 1, 2, 3, 4, 5, 6, 7, 8, 9, 10, 15, 20, 30, 35, 40, 45, 50, 55, or 60 minutes post-exposure, or may be administered to the subject 1, 2, 3, 4, 5, 6, 7, 8, 9, 10, 12, 20, 24, 48, 72 hours, or longer after being exposed to the filovirus or arenavirus.

Dosage

The pharmaceutical compositions of the invention are administered in such an amount as will be therapeutically effective, immunogenic, and/or protective against a pathogenic strain of a filovirus or arenavirus (e.g., at least $1 \times 10^3$ pfus/dose or between $1 \times 10^1$ and $1 \times 10^8$ pfus/dose). The dosage administered depends on the subject to be treated (e.g., the manner of administration and the age, body weight, capacity of the immune system, and general health of the subject being treated). The composition is administered in an amount to provide a sufficient level of expression that elicits an immune response without undue adverse physiological effects. A physician or researcher can decide the appropriate amount and dosage regimen.

In addition, single or multiple administrations of the compositions of the present invention may be given to a subject (e.g., one administration or administration two or more times). For example, subjects who are particularly susceptible to filovirus or arenavirus infection may require multiple treatments to establish and/or maintain protection against the virus. Levels of induced immunity provided by the pharmaceutical compositions described herein can be monitored by, e.g., measuring amounts of neutralizing secretory and serum antibodies. The dosages may then be adjusted or repeated as necessary to maintain desired levels of protection against viral infection.

EXAMPLES

The present invention is illustrated by the following example, which is in no way intended to be limiting of the invention.

Example 1

Construction of Recombinant Vectors and Virus

The rVSV expressing the glycoproteins (GP) of MARV strain Musoke (MARV-Musoke), Zaire ebolavirus strain Mayinga (ZEBOV), or Lassa virus strain Josiah were generated as described previously using the infectious clone for the VSV Indiana serotype (see, e.g., Garbutt et al., *J Virol.* 78: 5458-65, 2004, and Jones et al., *Nat Med* 11: 786-90, 2005). Specifically, a plasmid containing five VSV genes (nucleoprotein (N), phosphoprotein (P), matrix protein (M), glycoprotein (G), and polymerase (L)), flanked by the bacteriophage T7 promoter sequence, the VSV leader sequence, the hepatitis virus delta virus ribozyme sequence, and the T7 terminator sequence is employed. Between the G and L genes, a unique linker site (Xho-NheI) is present, flanked by a transcriptional start and stop signal for an additional gene to be expressed. The appropriate open reading frames encoding the glycoproteins were generated by PCR, cloned into the VSV genomic vectors lacking the VSV G gene, sequence confirmed, and rescued. For the challenge studies, the MARV-Musoke strain was used, isolated from a human case in 1980 in Kenya. ZEBOV (strain Kikwit) was isolated from a patient of the EBOV outbreak in Kikwit in 1995.

Example 2

Hemotology and Serum Biochemistry Analysis Performed in Animal Studies

Total white blood cell counts, lymphocyte counts, red blood cell counts, platelet counts, haematocrit values, total haemoglobin, mean cell volume, mean corpuscular volume, and mean corpuscular haemoglobin concentration were determined from animal blood samples collected in tubes containing EDTA, by using a laser-based haematology analyzer (Beckman Coulter). The white blood cell differentials were performed manually on Wright-stained blood smears. Serum samples were tested for concentrations of albumin, amylase, alanine aminotransferase, alkaline phosphatase, glucose, cholesterol, total protein, total bilirubin, urea nitrogen, and creatinine by using PICCOLO® Point-Of-Care blood analyzer (Abaxis).

Example 3

Virus Detection in Animal Studies

RNA was isolated from animal whole blood and swabs using appropriate RNA isolation kits (Qiagen). To detect VSV, an RT-PCR assay targeting the matrix gene (nucleotide position 2355-2661, NC_001560) was used. MARV RNA was detected by use of primer pairs targeting the L polymerase gene. The detection limit for this MARV assay is 0.1 plaque-forming units (pfu)/ml of plasma. The amount of infectious MARV was measured by plaque assay on Vero E6 cells from all blood samples. Briefly, increasing 10-fold dilutions of the samples were adsorbed to Vero E6 monolayers in duplicate wells (0.2 ml per well); thus, the limit for detection for this plaque assay was 25 pfu/ml. ZEBOV RNA was detected using primer pairs targeting the L genes (ZEBOV: RT-PCR, nucleotide position 13344-13622; nested PCR, nucleotide position 13397-13590). The sensitivity of the ZEBOV-specific RT-PCR is approximately 0.1 pfu/ml. ZEBOV titration was performed by plaque assay on Vero E6 cells from all blood and selected organ (e.g., adrenal, ovary, lymph nodes, liver, spleen, pancreas, lung, heart, and brain) and swab samples. Increasing 10-fold dilutions of the samples were adsorbed to Vero E6 monolayers in duplicate wells (0.2 ml per well); thus, the limit for detection for this plaque assay was 25 pfu/ml.

Example 4

Humoral Immune Response Analysis in Animal Studies

IgG and IgM antibodies against ZEBOV and MARV were detected with an enzyme-linked immunosorbent assay (ELISA) using purified virus particles as an antigen source. Neutralization assays were performed by measuring plaque reduction in a constant virus:serum dilution format, as known to one of skill in the art. Briefly, a standard amount of ZEBOV (100 pfu) or MARV (100 pfu) was incubated with serial 2-fold dilutions of the serum sample for 60 minutes. The mixture was used to inoculate Vero E6 cells for 60 minutes. Cells were overlayed with an agar medium, incubated for 8 days, and plaques were counted 48 hours after neutral red staining. End point titres were determined by the dilution of serum, which neutralized 50% of the plaques ($PRNT_{50}$).

Example 5

Cellular Immune Response Analysis in Animal Studies

Peripheral blood mononuclear cells were isolated from rhesus macaque whole blood samples by separation over a Ficoll gradient. Approximately $1 \times 10^6$ cells were stained for cell surface markers, granzyme B, and viral antigen using monoclonal antibodies. Cells were fixed and made permeable with FACS lyse (Becton Dickinson) supplemented with Tween-20 and stained with a mixture of antibodies against CD3, CD4, CD8, and either tumor necrosis factor α or interferon γ. Samples were run on a fluorescence-activated cell sorting analyzer (FACS Calibur, Becton Dickinson) and analyzed with software (FlowJo). Cytokine-positive cells were defined as a percentage in individual lymphocyte subsets, and at least 200,000 events were analyzed for every sample.

Example 6

Rhesus Macaque Studies Examining Post-Exposure Treatment for ZEBOV Infection Ten healthy adult *Macaca mulatta* of Chinese origin (3-6 kg) were used for this study. Briefly, all ten macaques were challenged by intramuscular (i.m.) inoculation with 1000 pfu of ZEBOV, strain Kikwit. Approximately 20-30 minutes after ZEBOV challenge, eight of the animals received an i.m. injection with a dose of $2\times10^7$ pfu of the VSVΔG/ZEBOVGP vector expressing the ZEBOV GP that was divided among four different anatomical locations (right and left triceps and right and left caudal thigh). Two animals served as experimental controls, of which one received an equivalent dose of the VSVΔG/MARVGP vector expressing the MARV GP and the other the VSVΔG/LASVGPC vector expressing the Lassa virus glycoprotein precursor by the same routes. All animals were checked twice daily for clinical symptoms of ZEBOV HF using an established score sheet. Swab samples (oral, nasal, and rectal) and blood were taken prior to ZEBOV challenge and on days 3, 6, and 10 post-ZEBOV challenge. Survivors were kept for more than 50 days. All nonhuman primate studies were performed in BSL-4 biocontainment at United States Army Medical Research Institute of Infectious Diseases (USAMRIID) and were approved by the USAMRIID Laboratory Animal Care and Use Committee. Animal research was conducted in compliance with the Animal Welfare Act and other Federal statues and regulations relating to animals; experiments involving animals adhere to the principles stated in the *Guide for the Care and Use of Laboratory Animals*, National Research Council, 1996. The facility used is fully accredited by the Association for Assessment and Accreditation of Laboratory Animal Care International.

Figure 2:
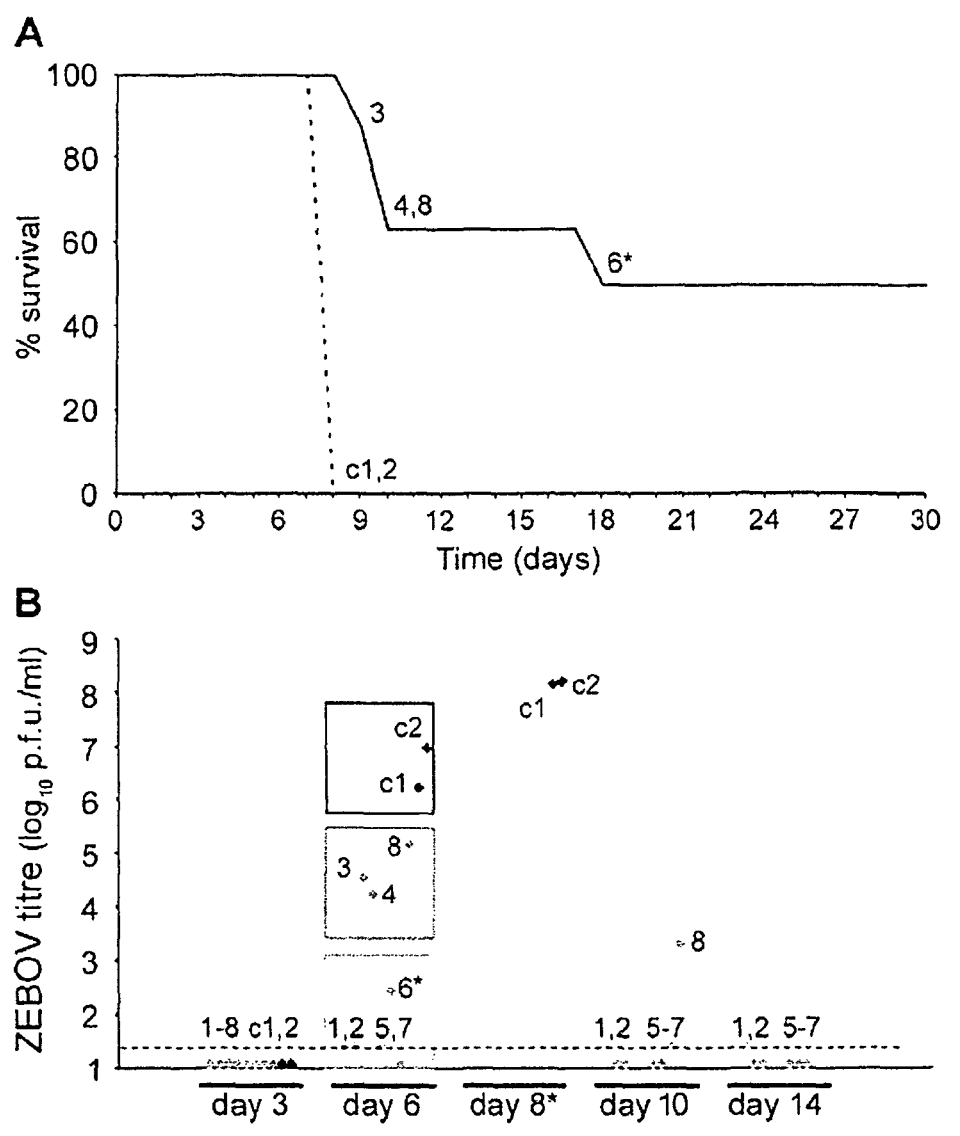

Eight rhesus monkeys (subjects 1 to 8) were treated with i.m. injections of the VSVΔG/ZEBOVGP vaccine ($2\times10^7$ pfu), and two rhesus monkeys (subjects c1 and c2) with VSV control vaccines ($2\times10^7$ pfu) 20 to 30 minutes after challenge with 1000 pfu of ZEBOV. The immunization and challenge doses were equivalent to what had been used in previous successful pre-exposure vaccine studies. All animals became febrile by day 6 and haematology data indicated evidence of illness by day 6, usually manifested as lymphopenia, in most of these animals (FIG. 1). Surprisingly, 50% of the VSVΔG/ZEBOVGP-treated animals (subjects 1, 2, 5, and 7) survived the lethal ZEBOV challenge (FIG. 1 and FIG. 2A) without showing signs of severe disease, while three VSVΔG/ZEBOVGP-treated macaques (subjects 3, 4, and 8) developed characteristic ZEBOV HF including fever, perturbations in clinical chemistry values, and macular rashes; these animals died on days 9 (subject 3) and 10 (subjects 4 and 8). Notably, all VSVΔG/ZEBOVGP-treated animals that succumbed to the ZEBOV challenge (subjects 3, 4, and 8) developed plasma viraemia on day 6 (between $1\times10^4$ and $1\times10^6$ pfu/ml), whereas plasma viraemia was transient in the animals that survived (subjects 1, 2, 5, and 7) and did not exceed $1\times10^2$ pfu/ml on day 6 (FIG. 2B). The final VSVΔG/ZEBOVGP-treated macaque (subject 6) died on day 18. This animal had a transient low-level ZEBOV viraemia on day 6 and had cleared the ZEBOV infection by day 10 (FIG. 2B). Furthermore, the animal never developed clinical symptoms consistent with severe ZEBOV HF, and organ infectivity titration showed no evidence of infectious ZEBOV in any of the tissues surveyed at post-mortem. Pathology results showed that this macaque died from disseminated septicaemia and peritonitis caused by *Streptococcus pneumoniae* as demonstrated by immunohistochemistry. The source of the bacterial infection is unknown. Both monkeys treated with the VSV control vectors (subjects c1 and c2) developed severe symptoms over the disease course with plasma viraemia titres in excess of $1\times10^6$ pfu/ml on day 6, macular rash, evident by day 7, and death on day 8 after ZEBOV challenge (FIG. 1 and FIG. 2A) with peak viraemia titre of $>1\times10^8$ pfu/ml (FIG. 2B). In addition, all animals were also tested for VSV viraemia using RT-PCR. VSV RNA was detected in most immunized animals only at day 3 post-immunization, indicating transient viraemia of the vaccine vector. There was no correlation between VSV viraemia and survival.

All four animals that survived the ZEBOV challenge (subjects 1, 2, 5, and 7) and the animal that survived until day 18 (subject 6) developed ZEBOV-specific humoral immune responses with low titre IgM antibodies detected on days 6-14 (subjects 1, 5, and 7) (FIG. 3A) and moderate IgG antibody titres detected on days 10-22 (subjects 1, 2, 5, 6, and 7) (FIG. 3B). Neutralizing antibody titres to ZEBOV (1:80) were detected on days 14-37 after challenge in all four animals that survived the ZEBOV challenge (subjects 1, 2, 5, and 7) and the animal that survived until day 18 (subject 6) (FIG. 3C). Humoral immune responses could not be detected in any of the non-survivors although these animals lived until day 9 and 10 post-challenge, which was sufficient to mount detectable IgM and IgG responses in the surviving animals.

The rhesus macaques that survived infection all controlled the virus within the first 6 days of infection. The data clearly show that moderate or high-level viraemia on day 6 invariably resulted in a fatal outcome (FIG. 2). Neutralizing antibodies were not essential for infection control since they were not detected until after the animals had cleared the EBOV infection. Circulating $CD4^+$ and $CD8^+$ T cells were reduced in number in all animals regardless of treatment. This indicates that the initial control of infection may not require classical T-cell responses. The time course for EBOV HF in rhesus macaques is very short (about 8 days) and, therefore, $CD8^+$ cytotoxic T-cell responses are very unlikely to be involved in the control of the infection because the cell numbers of specific responding cells could not have peaked until after the infection was controlled. The primary immune correlate of protection seems to be the rapid development of non-neutralizing antibody that was only seen in the protected animals (FIG. 3). This, coupled with the NK-cell increase in the VSVΔG/ZEBOVGP-treated animals, may have resulted in significantly enhanced killing of virus-infected primary target cells and, consequently, elimination of the ZEBOV infection. An important role of NK cells for protection has also been described for immunization with virus-like particles.

The adaptive response is essential to promote survival as animals immunized with the control VSV-based vaccines succumbed to the ZEBOV challenge. Both control animals died on day 8, which is the historical mean for rhesus monkeys infected by the same route and dose with this seed stock (historical n=23). However, other mechanisms probably contribute as well. Recently, a new paradigm for an interfering vaccine in which one of the antiviral mechanisms of action is intracellular interference with the replication of the lethal wild-type virus was described. In this example, the VSV vectors exploit the EBOV GP, which largely determines host cell tropism and mediates viral entry. It has been demonstrated that the VSV vectors expressing the ZEBOV GP will infect the same cells as wild-type ZEBOV in vitro. Also, the VSVΔG/ZEBOVGP vectors replicate significantly faster than wild-type ZEBOV. Therefore, it is possible that these vectors compete with ZEBOV through viral interference.

Clearly, even mild to moderate inhibition of ZEBOV replication may delay the course of infection and tip the balance in the favor of the host.

Example 7

Rhesus Macaque Studies Examining Post-Exposure Treatment for MARV Infection

Five rhesus macaques were challenged with MARV infection, as described above. Three of the five animals challenged with MARV and subsequently treated with the VSVΔG/MARVGP vectors became febrile by day 6; however, body temperatures returned to pre-challenge values by day 10. All five animals survived the MARV challenge. By contrast, one of the three control animals (treated with non-specific VSVΔG/ZEBOVGP vectors) developed a fever at day 6 and the remaining two control animals became febrile by day 10. Disease progression in these controls was consistent with MARV infection in rhesus macaques. All three control animals developed macular rashes by day 10 and succumbed to the MARV challenge, with two animals dying on day 11 and the remaining animal dying on day 12 (FIG. 4).

To determine whether viraemia of the rVSV vectors took place after treatment, whole blood samples from all eight treated animals were analyzed by RT-PCR. A transient rVSV viraemia was detected in four of the five VSVΔG/MARVGP-treated animals and two of the three control animals on day 3. MARV replication was also analyzed from blood samples taken after MARV challenge and rVSV vector treatment (FIG. 5). All three control animals developed high MARV titres by day 6 (about $10^3$ to $10^5$ pfu/ml). By contrast, no MARV was detected in plasma by plaque assay at any timepoint from the five animals treated with the VSVΔG/MARVGP vectors after MARV challenge. However, RT-PCR showed a transient MARV viraemia at day 3 in four of the five specifically treated animals.

With respect to the analysis of blood chemistry and hematology, no substantial changes (greater than a three-fold change compared with values before challenge) were detected in the five animals treated with the VSVΔG/MARVGP vectors during this study. However, the three control animals developed leucocytosis with concurrent neutrophilia at end-stage disease. Additionally, the three control animals showed substantial increases in circulating concentrations of alakine phosphatase, alanine aminotransferase, aspartate aminotransferase, γ glutamyltransferase, and total bilirubin at day 10, suggesting severe damage to the liver. Two control animals also showed substantial increases in concentrations of amylase at day 10, indicating possible injury of the kidneys and pancreas.

Figure 7:
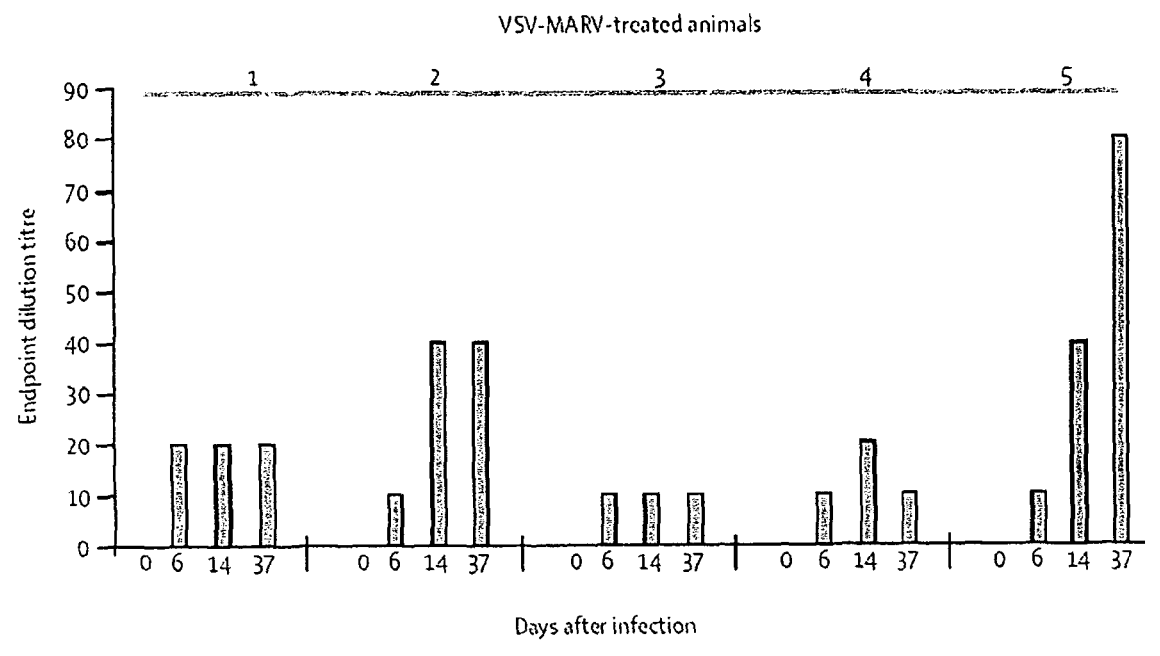

As shown by their serological response profiles after treatment, all five animals treated with VSVΔG/MARVGP vectors showed low to moderate amounts of IgM (endpoint dilution titres 1:32 to 1:100) by day 6 (FIG. 6); four of the five treated animals showed moderate amounts of IgG (greater than 1:100) by day 10 (FIG. 6). Plaque reduction neutralization tests showed low amounts of neutralizing antibodies (1:10 to 1:80) from day 6 to day 37 in the plasma of all five animals treated with VSVΔG/MARVGP (FIG. 7).

To better understand how T lymphocytes mediate protection against MARV challenge, FACS analysis was used. Intracellular staining of fractions of peripheral blood mononuclear cells showed an absence of interferon γ and tumor necrosis factor α induction in all animals, suggesting an absence of T-lymphocyte activation. The inability to detect a cellular immune response is consistent with previous investigations of the VSVΔG/MARVGP vectors as a preventative vaccine.

Use of the rVSV-based vector system as a countermeasure against MARV hemorrhagic fever shows dual efficacy, both as a potential preventative vaccine and as a possible post-exposure treatment. This example shows that rVSV-based vectors expressing the glycoprotein of MARV can mediate post-exposure protection against a homologous MARV challenge in non-human primates. The interval between MARV challenge and treatment was 20-30 minutes, which was chosen to represent a realistic amount of time that would be consistent with the treatment of an accidental needlestick exposure involving a laboratory or health-care worker.

The results of this example suggest that the VSVΔG/MARVGP vectors induce protection through responses to the surface glycoprotein, presumably by stimulation of glycoprotein-specific antibodies. Specifically, low concentrations of neutralizing antibodies and IgM were detected in serum samples 6 days after challenge, whereas increased amounts of anti-MARV IgG developed after 10-37 days. Although these data suggest that neutralizing antibodies could participate in post-exposure protection, the contribution of non-neutralizing antibodies and the therapeutic activity of antibody-mediated effector mechanisms likely play a more important role in protection.

OTHER EMBODIMENTS

All publications and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth.

What is claimed is:

1. A method of inhibiting or treating infection by Sudan species of Ebola virus (SEBOV) in a subject exposed to said SEBOV, said method comprising administering to said subject no later than 30 minutes after infection by said SEBOV a pharmaceutical composition comprising a recombinant viral vector that encodes at least a glycoprotein from said SEBOV, wherein the glycoprotein is heterologous to the viral vector.

2. The method of claim 1, wherein said composition comprises between $1 \times 10^1$ and $1 \times 10^8$ pfu of said viral vector.

3. The method of claim 1, wherein said viral vector is a vesicular stomatitis virus (rVSV) vector.

4. The method of claim 1, wherein said composition inhibits infection by said SEBOV.

5. The method of claim 1, wherein said composition alleviates at least one symptom associated with said SEBOV infection.

6. The method of claim 5, wherein said at least one symptom is hemorrhagic fever.

7. The method of claim 2, wherein said composition comprises at least $1 \times 10^3$ pfu of said viral vector.

8. The method of claim 1, wherein said composition induces an immune response against said SEBOV in said subject.

9. The method of claim 1, wherein said composition further comprises a pharmaceutically acceptable diluent, excipient, carrier, or adjuvant.

10. The method of claim 1, wherein said composition is formulated for administration by injection.

11. The method of claim 1, wherein said composition is formulated for administration two or more times.

12. The method of claim 1, wherein said subject is a human.

13. The method of claim 1, wherein said viral vector is selected from the group consisting of an adenovirus, rhabdovirus, and poxvirus vector.

* * * * *